(12) United States Patent
Kim et al.

(10) Patent No.: US 12,644,943 B2
(45) Date of Patent: Jun. 2, 2026

(54) APPARATUS AND METHOD FOR IMAGE RESTORATION OF ACCELERATED MRI BASED ON DEEP LEARNING

(71) Applicants: ClariPI Inc., Seoul (KR); Seoul National University R&DB Foundation, Seoul (KR)

(72) Inventors: Jong Hyo Kim, Seoul (KR); Hyun Sook Park, Seoul (KR); Tai Chul Park, Seoul (KR); Chul Kyun Ahn, Seoul (KR)

(73) Assignees: CLARIPI INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 1137 days.

(21) Appl. No.: 17/505,159

(22) Filed: Oct. 19, 2021

(65) Prior Publication Data

US 2022/0036512 A1    Feb. 3, 2022

Related U.S. Application Data

(63) Continuation of application No. PCT/KR2021/001097, filed on Jan. 27, 2021.

(30) Foreign Application Priority Data

Jan. 28, 2020    (KR) ........................ 10-2020-0009737
Jan. 26, 2021    (KR) ........................ 10-2021-0011052

(51) Int. Cl.
G01R 33/56        (2006.01)
A61B 5/055        (2006.01)
                     (Continued)

(52) U.S. Cl.
CPC .......... G01R 33/5608 (2013.01); A61B 5/055 (2013.01); G01R 33/4818 (2013.01); (Continued)

(58) Field of Classification Search
CPC .... G06T 5/00; G01R 33/4818; G01R 33/5608
See application file for complete search history.

(56) References Cited

U.S. PATENT DOCUMENTS

2019/0156524 A1*    5/2019    Park ......................... G06T 5/70
2019/0353741 A1    11/2019    Bolster, Jr. et al.
                   (Continued)

FOREIGN PATENT DOCUMENTS

KR        101312459        9/2013
KR        20140130784        11/2014
                   (Continued)

OTHER PUBLICATIONS

Wang et al., Accelerating Magnetic Resonance Imaging ViaDeep Learning, 2016 IEEE 13th International Symposium Onbiomedical Imaging (ISBI), Apr. 2016, pp. 514-517.

*Primary Examiner* — Benjamin O Dulaney
(74) *Attorney, Agent, or Firm* — CANTOR COLBURN LLP

(57)        ABSTRACT

Provided is a deep learning based accelerated MRI image quality restoring method. The deep learning based accelerated MRI image quality restoring method includes extracting test information from an input accelerated MRI image, selecting at least one deep learning model corresponding to the test information, among a plurality of previously trained deep learning models, and outputting an MRI image with a restored image quality for the input accelerated MRI image with the input accelerated MRI image as an input of at least one selected deep learning model.

8 Claims, 2 Drawing Sheets

(51) Int. Cl.
   *G01R 33/48*       (2006.01)
   *G01R 33/565*      (2006.01)

(52) U.S. Cl.
   CPC .................. *G01R 33/56545* (2013.01); *G06T*
        *2207/10088* (2013.01); *G06T 2207/20081*
                                    (2013.01)

(56)                References Cited

U.S. PATENT DOCUMENTS

| | | | |
|---|---|---|---|
| 2020/0034998 A1* | 1/2020 | Schlemper ............. | A61B 5/055 |
| 2020/0175675 A1 | 6/2020 | Ogino et al. | |
| 2020/0294287 A1* | 9/2020 | Schlemper ............. | A61B 5/055 |
| 2020/0341103 A1* | 10/2020 | Akcakaya ............. | G06N 3/084 |
| 2021/0090306 A1* | 3/2021 | Akcakaya .......... | G01R 33/5611 |

FOREIGN PATENT DOCUMENTS

| | | |
|---|---|---|
| KR | 20140141159 | 12/2014 |
| KR | 101697501 | 1/2017 |
| KR | 20190058285 | 5/2019 |
| WO | 2019026407 A1 | 2/2019 |

* cited by examiner

- 10
- EXTRACTING UNIT — 11
- SELECTING UNIT — 12
- OUTPUT UNIT — 13
- TRAINING UNIT — 14

START

EXTRACT TEST INFORMATION FROM INPUT ACCELERATED MRI IMAGE — S11

SELECT AT LEAST ONE DEEP LEARNING MODEL CORRESPONDING TO TEST INFORMATION — S12

OUTPUT MRI IMAGE WITH RESTORED IMAGE QUALIT — S13

END

APPARATUS AND METHOD FOR IMAGE RESTORATION OF ACCELERATED MRI BASED ON DEEP LEARNING

BACKGROUND

Field

The present disclosure relates to an apparatus and a method for restoring an image quality of an accelerated MRI image based on deep learning.

Description of the Related Art

When a high frequency is generated in a coil adjacent to a body in a state in which a subject enters a large circular machine with a magnetic field generator, the magnetic resonance imaging (hereinafter, abbreviated as "MRI") device measures a signal generated by resonance of hydrogen atomic nuclei in the body and reconstructs the signal by means of a computer as an image to obtain cross-sections of the human body in various directions.

The MRI image is harmless to the body unlike the X-ray computed tomography (CT) which is harmful to a human body due to the usage of X-rays. In addition, the CT mainly provides cross-sectional images, but the MRI is free in the direction and clearly shows a structure of soft tissues and characteristics of lesions so that it is widely utilized for complete medical checkup for organs and diseases.

A quality (a resolution and a precision) of an MRI image is a very important factor in precise diagnosis of lesions and efforts to improve the quality of the MRI image are continuing together with the development of the MRI system. For example, a high magnetic field generation technology and a high quality image reconstruction technology using multi-channel coils are regarded as such efforts.

However, most of the efforts of the related art to improve the quality of the MRI image requires a comparatively long scanning time so that it is difficult to actually apply it. Specifically, there are not many expensive MRI equipment installed and an operating cost is high so that when a long scanning time is used to acquire a high quality image, the test is piled up and the operating cost of the medical institutions is increased. Therefore, efforts to obtain a high quality image need to be accompanied by efforts to minimize the scanning time.

As an example of such efforts, MRI manufacturers are releasing high magnetic field multi-channel MRI systems. However, the high magnetic field multi-channel MRI system of the related art has problems in that the price is higher than that of the existing products and troubles to dispose the existing products are caused. As another example of the efforts, the MRI manufacturers acquire accelerated MRI images by upgrading hardware and software of the existing products of each manufacturer.

However, in this case, significant degradation in the image quality is accompanied so that a low quality MRI is obtained, which requires a solution. That is, more effective technique development which may acquire a high quality of diagnostic images while reducing an image acquiring time by means of accelerated scanning is required.

In the meantime, the deep learning technology is a new type of computing technique which achieves a specific purpose using a general-purpose program code which can be trained according to a given learning data set, instead of coding a series of detailed programs and its excellent performance is recognized in various image processing fields.

However, in order to show the desirable performance of the deep learning model, it is not only required to ensure enough training data sets, but also needed to be accompanied by a method of partitioning data to allow the deep learning model to be trained for data in a previously designated range and to be operated for data in the previously designated range even in an actual usage stage. In order to apply the deep learning to medical images in which safety is particularly important, it can be said that the development of the effective deep learning training technology which satisfies such prerequisites is even more important.

A background art of the present disclosure is disclosed in Korean Unexamined Patent Application Publication No. 10-2014-0130784.

SUMMARY

The present disclosure has been made an effort to solve the problems of the related art and an object of the present disclosure is to provide a deep learning based accelerated MRI image quality restoring apparatus and method which restore a low quality MRI image obtained by shortening a scanning time by means of accelerated scanning to a high quality image.

The present disclosure has been made an effort to solve the problems of the related art and an object of the present disclosure is to provide a training (learning) method of a deep learning model for a deep learning based MRI image quality restoring apparatus to more effectively apply the deep learning to medical images in which the safety is specifically important.

The present disclosure has been made an effort to solve the problems of the related art and an object of the present disclosure is to provide a deep learning based accelerated MRI image quality restoring apparatus and method and a training method of a deep learning model therethrough which ensure the performance and safety of the deep learning while utilizing the advantages of the deep learning.

However, technical objects to be achieved by various embodiments of the present disclosure are not limited to the technical objects as described above and other technical objects may be present.

As a technical means to achieve the above-described technical object, according to an aspect of the present disclosure, a deep learning based accelerated MRI image quality restoring method includes: extracting test information from an input accelerated MRI image, selecting at least one deep learning model corresponding to the test information, among a plurality of previously trained deep learning models, and outputting an MRI image with a restored image quality for the input accelerated MRI image with the input accelerated MRI image as an input of at least one selected deep learning model.

Further, according to an aspect of the present disclosure, the deep learning based accelerated MRI image quality restoring method further includes: before the extracting, generating a low quality of second MRI data set for training by applying an MRI image accelerated scanning simulator to a first MRI data set for training; extracting test information from the second MRI data set for training and grouping the second MRI data set for training into a plurality of groups according to a predetermined rule; and generating and training a plurality of deep learning models to be trained so as to correspond to each grouped second MRI data set for every group, and in the selecting, the plurality of previously trained deep learning models is a plurality of deep learning models to be trained which is trained by the training.

Further, in the generating, the MRI image accelerated scanning simulator performs: generating composite k-space data with an original image of the first MRI data set for training as an input, generating first low quality composite k-space data by applying a predetermined level of sub sampling to the composite k-space data, generating second low quality composite k-space data by adding a predetermined level of noise to the first low quality composite k-space data, generating a composite low quality MRI image based on the second low quality composite k-space data, and subtracting the original image from the generated composite low quality MRI image to generate a composite image quality degraded component MRI image.

Further, the second MRI data set for training is formed of a pair of a composite low quality MRI image and a composite image quality degraded component MRI image obtained based on an original image of the first MRI data set for training.

Further, in the training, in order to allow the plurality of deep learning models to be trained to have a function of extracting an image quality degraded component MRI image from the input MRI image input thereto, a composite accelerated MRI image for every MRI image is transmitted as an input of the deep learning model to be trained, in the grouped second MRI data set for training for every group and the deep learning model to be trained is repeatedly trained so as to minimize a difference between the composite image quality degraded component MRI image and the output of the deep learning model to be trained.

Further, in the outputting, at least one selected deep learning model extracts an image quality degraded component MRI image from the input accelerated MRI image with the input accelerated MRI image as an input of the at least one selected deep learning model and a predetermined value is multiplied with the extracted image quality degraded component MRI image to be subtracted from the input accelerated MRI image to output an MRI image with a restored image quality.

In the meantime, according to another aspect of the present disclosure, the deep learning based accelerated MRI image quality restoring apparatus includes: an extracting unit which extracts test information from an input accelerated MRI image; a selecting unit which selects at least one deep learning model corresponding to the test information, among a plurality of previously trained deep learning models; and an output unit which outputs an MRI image with a restored image quality for the input accelerated MRI image with the input accelerated MRI image as an input of at least one selected deep learning model.

Further, according to an aspect of the present disclosure, the deep learning based accelerated MRI image quality restoring apparatus further includes: a training unit which generates and trains a plurality of deep learning models to be trained, in which the training unit generates a second MRI data set for training with a low quality by applying an MRI image accelerated scanning simulator to a first MRI data set for training, extracts test information from the second MRI data set for training, groups the second MRI data sets for training into a plurality of groups according to a predetermined rule, and generates and trains a plurality of deep learning models to be trained so as to correspond to each of the grouped second MRI data set for training for every group, and the plurality of previously trained deep learning models may be the plurality of deep learning models to be trained which is trained by the training unit.

Further, the MRI image accelerated scanning simulator generates composite k-space data with an original image of the first MRI data set for training as an input, applies a predetermined level of sub sampling to the composite k-space data to generate first low quality composite k-space data, adds a predetermined level of noise to the first low quality composite k-space data to generate second low quality composite k-space data, generates a composite low quality MRI image based on the second low quality composite k-space data, and subtracts the original image from the generated composite low quality MRI image to generate a composite image quality degraded component MRI image.

Further, the second MRI data set for training is formed of a pair of a composite low quality MRI image and a composite image quality degraded component MRI image obtained based on an original image of the first MRI data set for training.

Further, in order to allow the plurality of deep learning models to be trained to have a function of extracting an image quality degraded component MRI image from the input MRI image input thereto, the training unit transmits a composite accelerated MRI image for every MRI image as an input of the deep learning model to be trained, in the grouped second MRI data set for training for every group and repeatedly trains the deep learning model to be trained so as to minimize a difference between the composite image quality degraded component MRI image and the output of the deep learning model to be trained.

Further, the output unit allows at least one selected deep learning model to extract an image quality degraded component MRI image from the input accelerated MRI image with the input accelerated MRI image as an input of the at least one selected deep learning model and multiplies a predetermined value with the extracted image quality degraded component MRI image to be subtracted from the input accelerated MRI image to output an MRI image with a restored image quality.

The above-described solving means are merely illustrative but should not be construed as limiting the present disclosure. In addition to the above-described embodiments, additional embodiments may be further provided in the drawings and the detailed description of the present disclosure.

According to the above-described solving means of the object of the present disclosure, the image quality of the accelerated MRI image is restored based on deep learning to acquire a high quality of diagnosis image (MRI image) while minimizing a scanning time.

According to the above-described solving means of the object of the present disclosure, the plurality of deep learning models (a plurality of deep learning models to be trained) is trained according to the test information of the MRI image to effectively apply the deep learning to a medical image in which the safety is specifically important.

According to the above-described solving means of the object of the present disclosure, a deep learning based MRI image quality restoring apparatus, method, and a deep learning model training (learning) method therethrough which ensure the performance of the deep learning and secure the safety while utilizing the advantages of the deep learning may be provided.

However, the effect which can be achieved by the present disclosure is not limited to the above-described effects, there may be other effects.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
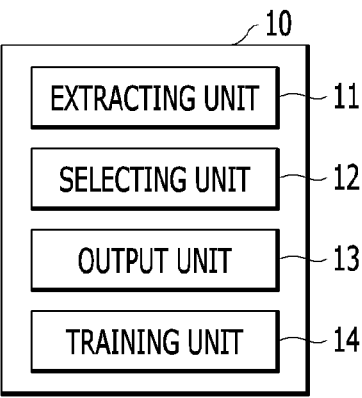
FIG. 1 is a view illustrating a schematic configuration of a deep learning based MRI image quality restoring apparatus according to an exemplary embodiment of the present disclosure.

Hereinafter, the present disclosure will be described more fully hereinafter with reference to the accompanying drawings to be easily implemented by those of ordinary skill in the art, in which exemplary embodiments of the present disclosure are shown. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

FIG. 1 is a view illustrating a schematic configuration of a deep learning based accelerated MRI image quality restoring apparatus according to an exemplary embodiment of the present disclosure. Hereinafter, the deep learning based accelerated MRI image quality restoring apparatus 10 according to an exemplary embodiment of the present disclosure is referred to as this apparatus 10 for the convenience of description.

Further, an input accelerated MRI image which will be described below is referred to as an input MRI image for the convenience of description.

Referring to FIG. 1, this apparatus 10 may include an extracting unit 11, a selecting unit 12, an output unit 13, and a training unit 14.

The extracting unit 11 may extract test information from the input accelerated MRI image (input MRI accelerated scanning image). According to an exemplary embodiment, the extracting unit 11 may extract the test information from header information included in the input MRI image. According to another exemplary embodiment, the extracting unit 11 may extract the test information by inputting the input MRI image in a predetermined classifier. In this case, the predetermined classifier extracts one or more predetermined image features from the input MRI image and allocates the image features to one of a predetermined number of categories. The test information may include test portion information and scan attribute information of the MRI image.

Here, the test portion information may refer to information about an organ part. That is, the test portion information refers to information about the organs of the human body of major interest, and may refer to, for example, information about organs such as head, chest, and abdomen. Further, the scan attribute information refers to information about MRI variables which influence on the characteristic of the MRI image and may refer to, for example, information such as a sequence type, a slice direction, the number of excitations (NEX), the number of phase encodings, a slice thickness, and the like.

The input MRI image may be an image acquired by a magnetic resonance imaging (MRI) device, but is not limited thereto and may be an image acquired by various imaging devices.

The selecting unit 12 may select at least one deep learning model corresponding to test information extracted from the extracting unit 11, among a plurality of previously-trained deep learning models.

The selecting unit 12 applies a predetermined rule (a rule determined in advance) to the extracted test information from the extracting unit 11 to select at least one (one or more) deep learning model corresponding to the test information extracted from the extracting unit 11, among the plurality of previously trained deep learning models.

According to this, this apparatus 10 may include a plurality of deep learning models. Here, each of the plurality of deep learning models is a deep learning model which has been trained in advance by the training unit 14 which will be described below and specifically, refers to a deep learning model which has been trained in advance so as to output an MRI image (a high quality MRI image) obtained by restoring an image quality of an MRI image (input MRI image) input to each deep learning model.

According to another exemplary embodiment, each of the plurality of deep learning models included in this apparatus 10 may refer to a deep learning model which has been trained in advance to extract an image quality degraded component MRI image from the MRI image input to each deep learning model (in other words, an input MRI image input to the deep learning model).

The plurality of deep learning models considered in this apparatus 10 may be generated by the training unit 14. The training unit 14 may generate a plurality of deep learning models according to the test information. Specifically, the training unit 14 may generate a plurality of deep learning models according to a combination of the test portion information and the scan attribute information of the MRI image included in the test information.

In other words, this apparatus 10 may include a plurality of deep learning models generated according to the test information (according to the combination of the test portion information and the scan attribute information). The plurality of deep learning models generated according to the combination of the test portion information and the scan attribute information may be trained using each training MRI data set (that is, an MRI data set for deep learning training) grouped according to the combination of the test portion information and the scan attribute information.

When the deep learning model is described in the present disclosure, a deep learning model before a training is performed by the training unit 14 may be referred to as a deep learning model to be trained. According to this, after completing the training for the deep learning model to be trained, it means a previously trained deep learning model. In other words, the plurality of previously trained deep learning models considered in the selecting unit 12 may refer to a plurality of deep learning models to be trained which has been trained by the training unit 14. The training of the deep learning model to be trained will be described in more detail below.

The selecting unit 12 may select at least one deep learning model corresponding to the test information extracted from the extracting unit 11 (corresponding to the combination of the test portion information and the scan attribute information extracted from the extracting unit) among the plurality of deep learning models which is generated according to the test information (according to the combination of the test portion information and the scan attribute information) and is trained in advance.

The selecting unit 12 may select at least one deep learning model which is suitable to apply an input MRI image, among a plurality of previously trained deep learning models, based on the test information extracted by the extracting unit 11.

For example, it is assumed that the input MRI image is a brain test MRI image which is an MRI image of a first test portion (for example, a brain) which is reconstructed with a first scan attribute (for example, a scan attribute of a T1w and a cross-sectional slice). In this case, the selecting unit 12 may select a single deep learning model (for example, a first deep learning model) trained with training data (an MRI data set for training) with a brain as a test portion and a scan attribute of T1w and a cross-sectional slice, as a deep learning model corresponding to the first scan attribute and the first test portion, among the plurality of previously trained deep learning models.

As another example, it is assumed that the input MRI image is a lumbar test MRI image which is an MRI image of a second test portion (for example, a lumbar) which is reconstructed with a second scan attribute (for example, a scan attribute of a T2w and a sagittal plane). In this case, the selecting unit 12 may select a single deep learning model (for example, a second deep learning model) trained with training data (an MRI data set for training) with a lumbar as a test site and a scan attribute of T2w and a sagittal plane, as a deep learning model corresponding to the second scan attribute and the second test portion, among the plurality of previously trained deep learning models.

As described above, the selecting unit 12 may select one or more deep learning models (at least one deep learning model) among the plurality of previously trained deep learning models in consideration of the combination of the test portion information and the scan attribute information included in the extracted test information, based on the test information extracted from the extracting unit 11.

The output unit 13 may output an MRI image obtained by restoring an image quality of the input MRI image with the input MRI image as an input of at least one deep learning model selected by the selecting unit 12. That is, the output unit 13 may input an input MRI image to at least one deep learning model selected by the selecting unit 12 and then output an MRI image obtained by restoring an image quality of the input MRI image through an output of at least one selected deep learning model.

The output unit 13 allows at least one selected deep learning model to extract an image quality degraded component MRI image from the input MRI image, with the input MRI image as an input of at least one deep learning model selected by the selecting unit 12 and multiplies a predetermined value (a predetermined ratio) with the image quality degraded component MRI image to be subtracted from the input MRI image to output an MRI image with a restored image quality from the input MRI image by means of at least one selected deep learning model.

As an example, it is assumed that a deep learning model selected by the selecting unit 12 is a single (one) deep learning model. In this case, the output unit 13 inputs the input MRI image to the single deep learning model selected by the selecting unit 12 to allow the single deep learning model to extract the image quality degraded component MRI image of the input MRI image and multiplies the predetermined ratio with the extracted image quality degraded component MRI image to be subtracted from the input MRI image, thereby outputting an MRI image with a restored image quality with respect to the input MRI image.

As another example, it is assumed that a plurality of deep learning models is selected by the selecting unit 12. In this case, the output unit 13 inputs the input MRI image to the plurality of deep learning models selected by the selecting unit 12 to allow the plurality of deep learning models to extract the image quality degraded component MRI image from the input MRI image input to the plurality of deep learning models and mixes a plurality of image quality degraded component MRI images extracted by the plurality of deep learning models according to a predetermined rule to subtract it from the input MRI image, thereby outputting an MRI image with a restored image quality with respect to the input MRI image.

The training unit 14 may generate and train the plurality of deep learning models to be trained before extracting the test information from the input MRI image in the extracting unit 11.

In this case, the training unit 14 generates a second MRI data set for training with a degraded quality by applying an MRI image accelerated scanning simulator to the first MRI data set for training, extracts test information from the second MRI data set for training, groups the second MRI data sets for training into a plurality of groups according to a predetermined rule, and generates and trains a plurality of deep learning models to be trained so as to correspond to each of the grouped second MRI data set for training for every group. The training unit 14 may individually train the plurality of generated deep learning models to be trained.

At this time, the plurality of deep learning models to be trained which is trained by the training unit 14 may refer to a plurality of previously trained deep learning models which is considered in the selecting unit 12.

Further, the MRI image accelerated scanning simulator which is considered when the second MRI data set for training is generated in the training unit 14 may generate composite k-space data with an original image of the first MRI data set for training as an input. Further, the MRI image accelerated scanning simulator may apply a predetermined level of sub sampling to the composite k-space data to generate first low quality composite k-space data.

Further, the MRI image accelerated scanning simulator adds a predetermined level of noise to the first low quality composite k-space data to generate second low quality composite k-space data and generate a composite low quality MRI image based on the second low quality composite k-space data.

The MRI image accelerated scanning simulator may generate a composite image quality degraded component MRI image by subtracting an original MRI image from the generated composite low quality MRI image.

Further, the second MRI data set for training which is considered in the training unit 14 may be formed of a pair of a composite low quality MRI image and a composite image quality degraded component MRI image obtained based on an original image of the first MRI data set for training (in other words, derived from the original image).

According to this, the training unit 14 may train the deep learning model to be trained using the pair of the composite high noise MRI image and the composite image quality degraded component MRI image obtained by applying the MRI image accelerated scanning simulator to the original image of the first MRI data set for training.

Further, in order to allow the plurality of deep learning models to be trained to have a function of extracting the image quality degraded component MRI image from the input MRI image input thereto, the training unit 14 transmits a composite low quality MRI image for every MRI image as an input of the deep learning model to be trained, in the grouped second MRI data set for training for every group, and repeatedly trains the deep learning model to be trained so as to minimize a difference between the composite image quality degraded component MRI image and the output of the deep learning model to be trained.

Hereinafter, the training unit 14 will be described in more detail.

The training unit 14 may train the deep learning model to be trained using an MRI data set for training (in other words, an MRI data set for deep learning training) generated by means of the MRI image accelerated scanning simulator, before extracting the test information from the input MRI image by the extracting unit 11. Here, the deep learning model to be trained may refer to at least one deep learning model.

The training unit 14 applies an original MRI image of the first MRI data set for training as an input of the MRI image accelerated scanning simulator to generate a second MRI data set for training with various levels of noises, before training the deep learning model to be trained. Next, the training unit 14 may train the deep learning model to be trained using the generated second MRI data set for training.

In this case, the training unit 14 may train the deep learning models to be trained corresponding to the deep learning models so as to allow the deep learning models included in this apparatus 10 to output a low noise MRI image with a reduced noise using the generated second MRI data set for training, with the low quality MRI image as an input. In other words, when the deep learning models included in this apparatus 10 receive the low quality MRI image by training the deep learning model to be trained by the training unit 14, the deep learning model may be trained to output a low noise input MRI image.

After generating the second MRI data set for training to which various levels of noises are added, the training unit 14 extracts the test information (test information including test portion information and scan attribute information) from the second MRI data set for training and groups the second MRI data set for training into a plurality of groups according to a predetermined rule. By doing this, a plurality of second MRI data set groups for training which is grouped according to the predetermined rule may include a second MRI data set for training for every test portion and a second MRI data set for training for every scan attribute information.

Specifically, when the MRI data set for training is generated, the training unit 14 may generate an MRI data set for training for every noise level. In other words, when the training unit 14 generates the second MRI data set for training to which various levels of noises are added, the training unit 14 may generate different second MRI data sets for training (second MRI data sets for deep learning training) depending on a plurality of predetermined noise levels.

Thereafter, the training unit 14 may extract the test information including the test portion information and the scan attribute information from the second MRI data set for training generated for every noise level. Thereafter, the training unit 14 may group the second MRI data sets for training into a plurality of groups according to the predetermined rule based on the extracted test information. Here, the predetermined rule may refer to a rule for dividing the MRI data (MRI images) included in the second MRI data sets for training generated for every noise level, for every predetermined test portion and/or every predetermined scan attribute.

By doing this, the training unit 14 may divide the second MRI data sets for training generated for every noise level, for every predetermined test portion and/or every predetermined scan attribute to be grouped into a plurality of groups. That is, a plurality of second MRI data set groups for training which is grouped by the grouping may include a second MRI data set for training for every test portion and a second MRI data set for training for every scan attribute.

Thereafter, the training unit 14 may generate a plurality of deep learning models to be trained so as to correspond to each of the second MRI data sets for training for every group which is grouped into a plurality of groups. That is, by doing this, the plurality of deep learning models to be trained generated by the training unit 14 may include a plurality of deep learning models to be trained generated for every test portion and a plurality of deep learning models to be trained generated for every scan attribute.

Thereafter, the training unit 14 may train the plurality of generated deep learning models for training with the second MRI data sets for training generated so as to correspond thereto.

That is, the training unit 14 may train each of the deep learning models to be trained generated for every test portion using the MRI data set for training generated for every test portion. Further, the training unit 14 may train each of the deep learning models to be trained generated for every scan attribute using the MRI data set for training generated for every scan attribute.

In other words, the training unit 14 may train each of the deep learning models to be trained generated for every test portion using corresponding MRI data sets for training generated for every test portion. Further, the training unit 14 may train each of the deep learning models to be trained generated for every scan attribute using corresponding MRI data sets for training generated for every scan attribute.

By doing this, the training unit 14 may train each of the plurality of deep learning models to be trained (a plurality of deep learning models) using the plurality of MRI data sets for training generated for every test portion and every scan attribute (that is, second MRI data sets for training for every group which are grouped into a plurality of groups) so as to allow each of the plurality of deep learning models to be trained (the plurality of deep learning models) included in this apparatus 10 generated for every test portion and every scan attribute to output a low noise MRI image with a reduced noise with a low quality MRI image as an input.

After generating the plurality of deep learning model to be trained so as to correspond to each of second MRI data sets for training for every group which is grouped into a plurality of groups, the training unit 14 may train the plurality of deep learning models to be trained using the MRI data set for training generated so as to correspond thereto.

When each of the plurality of deep learning models included in this apparatus 10 receives a low quality MRI image as an input MRI image, the plurality of deep learning models may be trained (learned) to output the low noise input MRI image with a reduced nose with respect to the low quality MRI image, by means of the training by the training unit 14.

In other words, the training unit 14 receives an original MRI image using the MRI image accelerated scanning simulator to generate different MRI data sets for training (second MRI data sets for training for every noise level) according to a plurality of noise levels.

Thereafter, the training unit 14 may group the MRI data sets for training generated, for example, for every noise level into a plurality of groups for every scan attribute. That is, the training unit 14 may generate a plurality of MRI data set groups for training including the MRI data set for training for every scan attribute based on the MRI data set for training generated for every noise level.

Next, the training unit 14 may generate a plurality of deep learning models to be trained for every scan attribute as a deep learning model to be trained included in this apparatus 10 so as to correspond to each of the second MRI data set for training generated , for example, for every scan attribute.

Next, the training unit 14 may train each of the deep learning models to be trained generated for every scan attribute using the MRI data set for training (an MRI data set for training for every scan attribute) generated so as to correspond to the corresponding scan attribute. In this case, when the input MRI image is given as an input, the training unit 14 may train each of the plurality of deep learning models to be trained generated for every scan attribute so as to allow the deep learning model (a deep learning model to be trained) corresponding to a scan attribute of the input MRI image to output a low noise MRI image with the input MRI image as an input.

By doing this, when an input MRI image is given in this apparatus 10, the selecting unit 12 may select a deep learning model corresponding to the scan attribute of the input MRI image so as to operate a corresponding deep learning model according to the scan attribute of the input MRI image, among the plurality of previously trained deep learning models and then the output unit 13 may output an input MRI image with a restored image quality using the selected deep learning model.

Further, the training unit 14 receives an original MRI image using the MRI image accelerated scanning simulator to generate different MRI data sets for training (second MRI data sets for training for every noise level) according to a plurality of noise levels.

Thereafter, the training unit 14 may group the MRI data sets for training generated, for example, for every noise level into a plurality of groups for every test portion. That is, the training unit 14 may generate a plurality of MRI data set groups for training including the MRI data set for training for every test portion based on the MRI data set for training generated for every noise level.

Thereafter, the training unit 14 may generate a plurality of deep learning models to be trained, for example, for every test portion as a deep learning model to be trained included in this apparatus 10 so as to correspond to each of the second MRI data set for training generated for every test portion.

Thereafter, the training unit 14 may train each of the deep learning models to be trained generated for every test portion using the MRI data set for training (an MRI data set for training for every test portion) generated so as to correspond to the corresponding test portion. In this case, when the input MRI image is given, the training unit 14 may train each of the plurality of deep learning models to be trained generated for every test portion so as to allow the deep learning model (a deep learning model to be trained) corresponding to a test portion of the input MRI image to output a low noise MRI image with the input MRI image as an input.

By doing this, when an input MRI image is given in this apparatus 10, the selecting unit 12 may select a deep learning model corresponding to the test portion of the input MRI image so as to operate a corresponding deep learning model according to the test portion of the input MRI image, among the plurality of previously trained deep learning models and then the output unit 13 may output an input MRI image with an image quality restored using the selected deep learning model.

That is, the MRI data set for training for every test portion and/or every scan attribute may be generated and the deep learning model to be trained for every test portion and/or every scan attribute may be generated and trained, by the training unit 14.

Further, the MRI data set for training generated by the training unit 14 may include at least one pair of an original MRI image, a composite low quality MRI image, and a composite image quality degraded component MRI image. In other words, the training unit 14 may generate an MRI data set for training (a second MRI data set for training) including at least one pair of the original MRI image, the composite low quality MRI image, and the composite image quality degraded component MRI image, with the original MRI image as an input of the MRI image accelerated scanning simulator.

The second MRI data set for training which is considered in the training unit 14 may be formed of a pair of a composite low quality MRI image and a composite image quality degraded component MRI image derived from an original image of the first MRI data set for training.

The training unit 14 may transmit the composite low quality MRI image as an input of the deep learning model to be trained and repeatedly train the deep learning model to be trained so as to minimize the difference between the composite image quality degraded component MRI image and the output of the deep learning model to be trained, for every MRI image.

That is, in order to allow each of the plurality of deep learning models to be trained to have a function of extracting the image quality degraded component MRI image from the input MRI image input thereto, the training unit 14 may transmit a composite low quality MRI image for every MRI image to an input of the deep learning model to be trained, in the grouped second MRI data set for training for every group and repeatedly train the plurality of deep learning models to be trained so as to minimize a difference between the composite image quality degraded component MRI image and the output of the deep learning model to be trained.

In other words, the training unit 14 may transmit the composite low quality MRI image to the input of the deep learning model to be trained, for every MRI image, in the second MRI data set for training divided into groups and repeatedly train the deep learning model to be trained so as to minimize the difference between the composite image quality degraded component MRI image and the output of the deep learning model to be trained so that the deep learning model to be trained may have a function of extracting an image quality degraded component from the MRI image.

Further, the MRI image accelerated scanning simulator which is used for training in the training unit 14 may generate composite k-space data with an original MRI image of the first MRI data set for training as an input. Further, the MRI image accelerated scanning simulator may generate a low quality of first composite k-space data by applying a predetermined level of sub sampling to the generated composite k-space data. Further, the MRI image accelerated scanning simulator may generate a low quality of second composite k-space data by adding a predetermined noise to the low quality of generated first composite k-space data. Further, the MRI image accelerated scanning simulator may generate a low quality of composite accelerated MRI image based on the second composite k-space data. Further, the MRI image accelerated scanning simulator may generate a composite image quality degraded component MRI image by subtracting an original MRI image from the generated low quality MRI image.

As a specific example, the MRI image accelerated scanning simulator may generate composite k-space data with an original MRI image of the first MRI data set for training as an input. For example, the MRI image accelerated scanning simulator performs an inversion Fourier transform after inputting the original MRI image to a magnitude component of a Fourier domain and inputting "0" to a phase component of the Fourier domain to generate composite k-space data for the original image.

Thereafter, the MRI image accelerated scanning simulator adds a predetermined level of sub sampling by applying an MRI image physical principle (that is, a physical principle of the MRI image) to the generated composite k-space data to generate the low quality composite k-space data. Further, the MRI image accelerated scanning simulator may generate a predetermined level of noise component k-space data by applying the MRI image physical principle (that is, the physical principle of the MRI image).

Thereafter, the MRI image accelerated scanning simulator may add noise component k-space data to the sub-sampled composite low quality k-space data and generate a low quality composite MRI image based thereon. For example, the MRI image accelerated scanning simulator may perform Fourier transform on the composite k-space data and take a magnitude component to generate a composite low quality MRI image.

In this case, when the sub-sampling of the composite k-space data is applied, the MRI image accelerated scanning simulator may determine a sub-sampling direction, a sub-sampling ratio, and a sub-sampling manner of the composite k-space data based on the test information of the original MRI image. For example, when a phase encoding direction in the test information of the original MRI image is a row direction, a sub-sampling direction is set to a column direction and when the phase encoding direction of the information is a column direction, the sub-sampling direction is set to a row direction.

As described above, this apparatus 10 may train each of the plurality of deep learning models (that is, a plurality of deep learning models to be trained) by means of the training unit 14 so as to allow the plurality of deep learning models included in this apparatus 10 to output a high quality MRI image with a restored image quality with respect to an MRI image input to each deep learning model.

Based on the plurality of deep learning models which has been trained in advance (a plurality of deep learning models to be trained which is trained by the training unit) as described above, this apparatus 10 may select a corresponding deep learning model from the plurality of previously trained deep learning models in consideration of the test information extracted from the input MRI image.

Thereafter, this apparatus 10 may output an input image with a restored image quality (that is, a high quality input MRI image) with respect to the input MRI image from the selected deep learning model by providing the input MRI image to the selected deep learning model as an input.

The present disclosure may provide a deep learning based MRI image quality restoring apparatus (this apparatus, 10) which outputs a high quality MRI image with a restored image quality (a high quality input MRI image) from the input of a low quality (a resolution and a noise) of input MRI image (for example, accelerated input MRI image), based on the plurality of previously trained deep learning models.

The input MRI image with a restored image quality which is output from this apparatus 10 may have a quality which is equal to or higher than a quality of the precisely scanned MRI image.

Further, this apparatus 10 provides a training (learning) method of the deep learning model (a deep learning model to be trained) to output a high quality MRI image with a restored image quality from an input of a low quality of input MRI image and the input MRI image with a restored image quality output by the deep learning model trained as described above (that is, a previously trained deep learning model) may have a quality which is equal to or higher than a quality of the precisely scanned MRI image.

This apparatus 10 may extract test portion information and scan attribute information as test information from the input MRI image using medical information included in the input MRI image using the extracting unit 11.

Thereafter, this apparatus 10 may select a deep learning model corresponding to the extracted test information (that is, a deep learning model which has been trained in advance to show a predetermined level of performance) from a plurality of previously trained deep learning models and output (acquire) an input MRI image with an image quality restored by the selected deep learning model.

This apparatus 10 may train each of the plurality of deep learning models to be trained by means of the training unit 14 to allow the plurality of deep learning models to show a predetermined level of performance (a level of minimizing a difference between the image quality degraded component MRI image and an output of the deep learning model to be trained).

Further, this apparatus 10 receives the original MRI image to generate the MRI data set for training including the composite low quality component MRI image using the MRI accelerated scanning simulator and trains the deep learning model to be trained included in this apparatus 10 using the generated MRI data set for training.

The deep learning model to be trained included in this apparatus 10 may be a deep learning model which has been trained in advance by means of the training using the MRI data set for training and such a previously trained deep learning model may refer to a deep learning model which has been trained in advance to output an MRI image with a restored image quality (a high quality MRI image) from the low quality MRI image.

Further, this apparatus 10 trains the deep learning model to be trained with the MRI data set for training generated using the MRI accelerated scanning simulator so that when the low quality MRI image (input MRI image) acquired during the actual accelerated scanning is used as an input of this apparatus 10 (that is, used as an input of at least one deep learning model among the plurality of previously trained deep learning models included in this apparatus), this apparatus may output a high quality MRI image with an image quality which is more effectively restored with respect to the low quality MRI image.

The plurality of deep learning models generated for every test portion and every scan attribute, included in this apparatus 10, may be trained by the training unit 14 to output an MRI image with restored image quality with respect to the original MRI image input thereto.

This apparatus 10 may also be represented not only as a deep learning based MRI image quality restoring apparatus, but also as a deep learning model (a deep learning model to be trained) training apparatus for restoring an MRI image quality based on deep learning. The present disclosure may provide not only a deep learning based MRI image quality restoring method, but also a deep learning model training method for restoring an MRI image quality based on deep learning, by means of this apparatus 10.

Hereinafter, an operation flow of the present disclosure will be described in brief based on the above detailed description.

Figure 2:
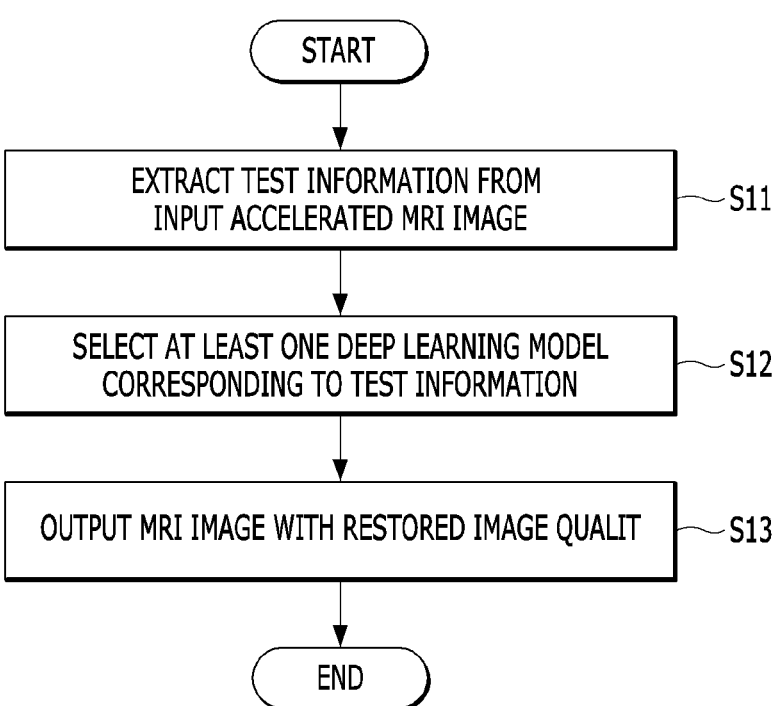
FIG. 2 is a view illustrating a schematic operation flow for a deep learning based MRI image quality restoring method by a deep learning based MRI image quality restoring apparatus according to an exemplary embodiment of the present disclosure.

FIG. 2 is a view illustrating a schematic operation flow for a deep learning based MRI image quality restoring method by a deep learning based MRI image quality restoring apparatus according to an exemplary embodiment of the present disclosure.

The deep learning based MRI image quality restoring method illustrated in FIG. 2 may be performed by the above-described deep learning based MRI image quality restoring apparatus (this apparatus, 10). Accordingly, even though description is omitted, the description for the deep learning based MRI image quality restoring apparatus (this apparatus, 10) may also be applied to the description for the deep learning based MRI image quality restoring method in the same manner.

Referring to FIG. 2, in a deep learning based MRI image quality restoring method according to an exemplary embodiment of the present disclosure, in step S11, the extracting unit 11 may extract test information from an input accelerated MRI image (an input MRI image).

Next, in step S12, the selecting unit 12 may select at least one deep learning model corresponding to test information extracted in step S11, among a plurality of previously trained deep learning models.

Next, in step S13, the output unit 13 may output an MRI image obtained by restoring an image quality of the input MRI image with the input MRI image as an input of at least one deep learning model selected in step S12.

In this case, in step S13, the output unit 13 allows at least one deep learning model selected in step S12 to extract an image quality degraded component MRI image from the input MRI image, with the input MRI image as an input of at least one deep learning model selected in step S12 and multiplies a predetermined value (for example, a predetermined ratio) with the image quality degraded component MRI image to be subtracted from the input MRI image to output an MRI image with a restored image quality with respect to the input MRI image.

In the meantime, the deep learning based MRI image quality restoring method according to the exemplary embodiment of the present disclosure may further include a step of generating and training a plurality of deep learning models to be trained before step S11. At this time, the plurality of deep learning models to be trained which is trained by the training step may refer to a plurality of previously trained deep learning models which is considered in step S12.

Figure 3:
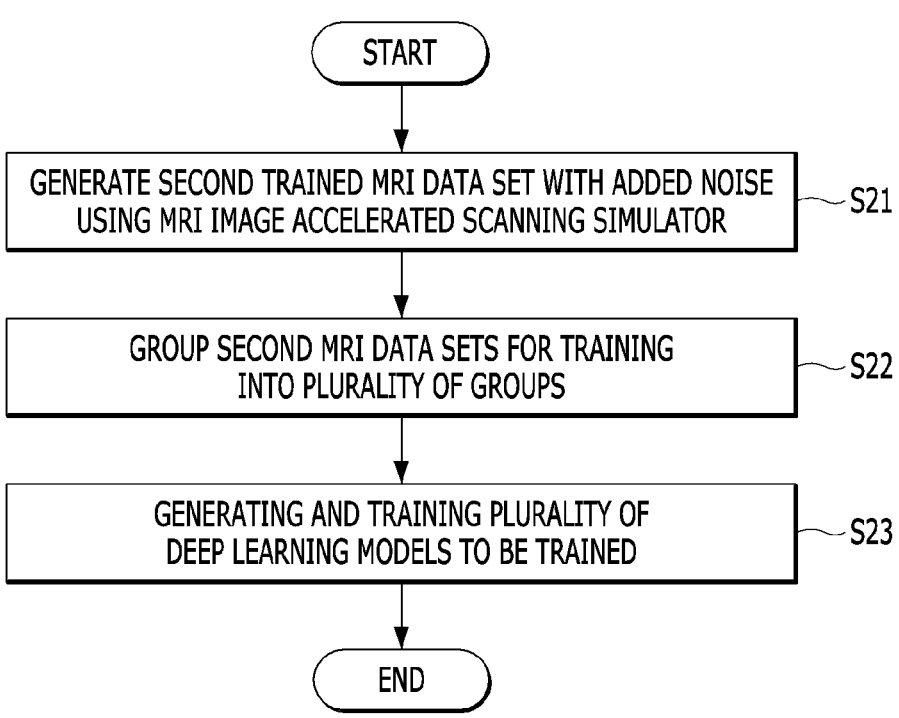
FIG. 3 is a view illustrating an example of a schematic operation flow for a deep learning model training method for restoring an MRI image quality based on deep learning by a deep learning based MRI image quality restoring apparatus according to an exemplary embodiment of the present disclosure.

In this case, the description of the method of training the plurality of deep learning models to be trained, that is, the method for training a deep learning model may be more easily understood with reference to the following FIG. 3.

In the above-description, steps S11 to S13 may be further divided into additional steps or combined as smaller steps depending on an implementation example of the present disclosure. Further, some steps may be omitted if necessary and the order of steps may be changed.

FIG. 3 is a view illustrating an example of a schematic operation flow for a deep learning model training method for restoring an MRI image quality based on deep learning by a deep learning based MRI image quality restoring apparatus according to an exemplary embodiment of the present disclosure. That is, FIG. 3 is a view illustrating an example of a schematic operation flow of a method of training a deep learning model to be trained considered in the present disclosure.

The deep learning model training method for restoring the MRI image quality based on deep learning illustrated in FIG. 3 may be performed by the above-described deep learning based MRI image quality restoring apparatus (this apparatus, 10). Accordingly, even though description is omitted, the description for the deep learning based MRI image quality restoring apparatus (this apparatus, 10) may also be applied to the description for the deep learning model training method for restoring the MRI image quality based on deep learning in the same manner.

Referring to FIG. 3, in step S21, the training unit 14 may input the input MRI image to the MRI image accelerated scanning simulator to train the deep learning models included in this apparatus 10 before the extracting unit 11 extracts test information from the input MRI image in the above-described step S11 of FIG. 2.

That is, in step S21, the training unit 14 may provide the input MRI image as an input of the MRI image accelerated scanning simulator.

Specifically, in step S21, the MRI image accelerated scanning simulator may generate composite k-space data with an original image of the first MRI data set for training as an input. Further, the MRI image accelerated scanning simulator may apply a predetermined level of sub sampling to the generated composite k-space data to generate a low quality of first composite k-space data.

Further, the MRI image accelerated scanning simulator may generate a low quality of second composite k-space data by adding a predetermined noise to the low quality of generated first composite k-space data. Further, the MRI image accelerated scanning simulator may generate a low quality of composite accelerated MRI image based on the second composite k-space data. Further, the MRI image accelerated scanning simulator may generate a composite image quality degraded component MRI image by subtracting an original MRI image from the generated composite low quality MRI image.

By doing this, in step S21, the training unit 14 may generate a second MRI data set for training with various levels of noises by applying the MRI image accelerated scanning simulator to the first MRI data set for training, before the extracting unit 11 extracts the test information from the input MRI image.

That is, in step S21, the training unit 14 receives the original image using the MRI image accelerated scanning simulator to generate different MRI data sets for training according to the plurality of noise levels.

Here, the second MRI data set for training may be formed of a pair of a composite low quality MRI image and a composite image quality degraded component MRI image obtained based on an original image of the first MRI data set for training (derived from the original image).

The training unit 14 may train the deep learning to be trained using the pair of the composite low quality MRI image and the composite image quality degraded component MRI image obtained by applying the MRI image accelerated scanning simulator to the original image of the first MRI data set for training.

Next, in step S22, the training unit 14 extracts test information from the second MRI data set for training and groups the second MRI data sets for training into a plurality of groups according to a predetermined rule.

In this case, in step S22, the training unit 14 groups second MRI data sets into a plurality of groups to generate MRI data sets for training for every test portion and/or every scan attribute.

Next, in step S23, the training unit 14 generates and trains a plurality of deep learning models to be trained so as to correspond to the plurality of second MRI data set groups for training generated in step S22. That is, in step S23, the training unit 14 generates and trains a plurality of deep learning models to be trained so as to correspond to each of the second MRI data sets which is grouped by step S22.

Specifically, in step S23, the training unit 14 may generate a deep learning model for training for every test portion corresponding to each MRI data set for training generated for every test portion. Further, the training unit 14 may generate and train the deep learning models to be trained for every scan attribute corresponding to the MRI data set for training generated for every scan attribute.

In step s23, the training unit 14 may train the plurality of deep learning models to be trained generated in step S23 using the plurality of MRI data sets for training (that is, a plurality of MRI data set groups for training) generated in step S22.

As a specific example, in step S23, the training unit 14 may train each deep learning model trained for every test portion and/or every scan attribute generated in step S23 so as to correspond to the MRI data set generated for every test portion and/or the scan attribute in step S22 using the same.

Further, in step S23, in order to allow the plurality of deep learning models to be trained to have a function of extracting the image quality degraded component MRI image from the input MRI image input thereto, the training unit 14 transmits a composite low quality MRI image for every MRI image as an input of the deep learning model to be trained, in the second MRI data set for training for every group grouped in step S22 and repeatedly trains the deep learning model to be trained so as to minimize a difference between the composite image quality degraded component MRI image and the output of the deep learning model to be trained.

In other words, the training unit 14 transmits a composite low quality MRI image for every input MRI image as an input of each of the plurality of deep learning models to be trained and repeatedly trains each of the plurality of deep learning models to be trained so as to minimize a difference between the composite image quality degraded component MRI image and the output of the deep learning model to be trained.

In step S23, the training unit 14 may repeatedly train each of the deep learning models to be trained generated for every test portion using the MRI data set for training generated for every test portion. Further, the training unit 14 may repeatedly train each of the deep learning models to be trained generated for every scan attribute using the MRI data set for training generated for every scan attribute.

By doing this, the plurality of deep learning models to be trained considered in this apparatus 10 may include a deep learning model to be trained generated for every test portion and a deep learning model to be trained generated for every scan attribute.

In the above-description, steps S21 to S23 may be further divided into additional steps or combined as smaller steps depending on an implementation example of the present disclosure. Further, some steps may be omitted if necessary and the order of steps may be changed.

The deep learning based MRI image quality restoring method and the deep learning model training method for restoring an MRI image quality based on deep learning according to the exemplary embodiment of the present disclosure may be implemented in the form of a program command which can be executed by various computer units to be recorded in a computer readable medium. The computer readable medium may include solely a program instruction, a data file, and a data structure or a combination thereof. The program instruction recorded in the medium may be specifically designed or constructed for the present invention or known to those skilled in the art of a computer software to be used. Examples of the computer readable recording medium include a magnetic media such as a hard disk, a floppy disk, or a magnetic tape, an optical media such as a CD-ROM or a DVD, a magneto-optical media such as a floptical disk, and a hardware device which is specifically configured to store and execute the program instruction, such as a ROM, a RAM, and a flash memory. Examples of the program instruction include not only a machine language code which is created by a compiler but also a high level language code which may be executed by a computer using an interpreter. The hardware device may operate as one or more software modules in order to perform the operation of the present invention and vice versa.

Further, the above-described deep learning based MRI image quality restoring method and the deep learning model training method for restoring an MRI image quality based on deep learning may be implemented in the form of a computer program or an application executed by a computer which is stored in a recording medium.

The above-description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

What is claimed is:

1. A deep learning based accelerated MRI image quality restoring method, the method comprising:

generating a low quality of second MRI data set for training by applying an MRI image accelerated scanning simulator to a first MRI data set for training;

extracting test information from the second MRI data set for training and grouping the second MRI data set for training into a plurality of groups according to a predetermined rule;

generating and training a plurality of deep learning models to be trained so as to correspond to each grouped second MRI data set for every group;

extracting test information from an input accelerated MRI image;

selecting at least one deep learning model corresponding to the test information, among a plurality of previously trained deep learning models; and outputting an MRI image with a restored image quality with respect to the input accelerated MRI image with the input accelerated MRI image as an input of at least one selected deep learning model, wherein in the selecting, the plurality of previously trained deep learning models is a plurality of deep learning models to be trained which is trained by the training, and wherein in the generating step, the MRI image accelerated scanning simulator performs:

generating composite k-space data with an original image of the first MRI data set for training as an input;

generating first low quality composite k-space data by applying a predetermined level of sub sampling to the composite k-space data;

generating second low quality composite k-space data by adding a predetermined level of noise to the first low quality composite k-space data;

generating a composite low quality MRI image based on the second low quality composite k-space data; and subtracting the original image from the generated composite low quality MRI image to generate a composite image quality degraded component MRI image.

2. The restoring method according to claim 1, wherein the second MRI data set for training is formed of a pair of the generated composite low quality MRI image and the composite image quality degraded component MRI image obtained based on an original image of the first MRI data set for training.

3. A non-transitory computer readable recording medium in which a program allowing a computer to execute the method according to claim 2 is recorded.

4. The restoring method according to claim 1, wherein in the training, in order to allow the plurality of deep learning models to be trained to have a function of extracting an image quality degraded component MRI image from the input accelerated MRI image input thereto, a composite accelerated MRI image for every MRI image is transmitted as an input of the deep learning models to be trained, in the grouped second MRI data set for training for every group, and the deep learning models to be trained is repeatedly trained so as to minimize a difference between the composite image quality degraded component MRI image and the output of the deep learning models to be trained.

5. A non-transitory computer readable recording medium in which a program allowing a computer to execute the method according to claim 4 is recorded.

6. The restoring method according to claim 1, wherein in the outputting, at least one selected deep learning model extracts an image quality degraded component MRI image from the input accelerated MRI image with the input accelerated MRI image as an input of at least one selected deep learning model and a predetermined value is multiplied with the extracted image quality degraded component MRI image to be subtracted from the input accelerated MRI image to output an MRI image with a restored image quality.

7. A non-transitory computer readable recording medium in which a program allowing a computer to execute the method according to claim 6 is recorded.

8. A non-transitory computer readable recording medium in which a program allowing a computer to execute the method according to claim 1 is recorded.

* * * * *